United States Patent [19]

White

[11] 4,263,922
[45] Apr. 28, 1981

[54] METHOD AND DEVICE FOR COLLECTING, TRANSPORTING, AND DELIVERING MICRO SAMPLES OF BLOOD

[75] Inventor: Fred K. White, Miami, Fla.

[73] Assignee: American Hospital Supply Corporation, Evanston, Ill.

[21] Appl. No.: 71,702

[22] Filed: Aug. 31, 1979

[51] Int. Cl.³ .............................................. A61B 5/14
[52] U.S. Cl. ................................ 128/763; 73/425.4 P
[58] Field of Search ....................... 128/763, 768, 770; 73/425.4 P, 425.4 R

[56] References Cited

U.S. PATENT DOCUMENTS

| | | | |
|---|---|---|---|
| 3,645,252 | 2/1972 | Gilford | 128/764 |
| 3,977,403 | 8/1976 | Patel | 128/274 X |
| 4,133,304 | 1/1979 | Bailey | 128/764 |
| 4,187,860 | 2/1980 | Villari | 128/763 |

Primary Examiner—Kyle L. Howell
Attorney, Agent, or Firm—Tilton, Fallon, Lungmus

[57] ABSTRACT

A method for collecting micro samples of arterial or venous blood from patients and for transporting and delivering such samples to suitable blood analysis equipment such as a conventional blood gas analyzer. An essential component of the device is a tubular elastomeric adapter-handle having integral body and tip sections, the body section having a tapered bore for receiving and holding the end portion of a heparinized glass microcapillary tube and the tip being both internally and externally tapered (in reverse directions) to permit releasable attachment of the tip to the hub of a hypodermic needle and, after a sample has been collected, to the inlet of a blood analyzer.

11 Claims, 8 Drawing Figures

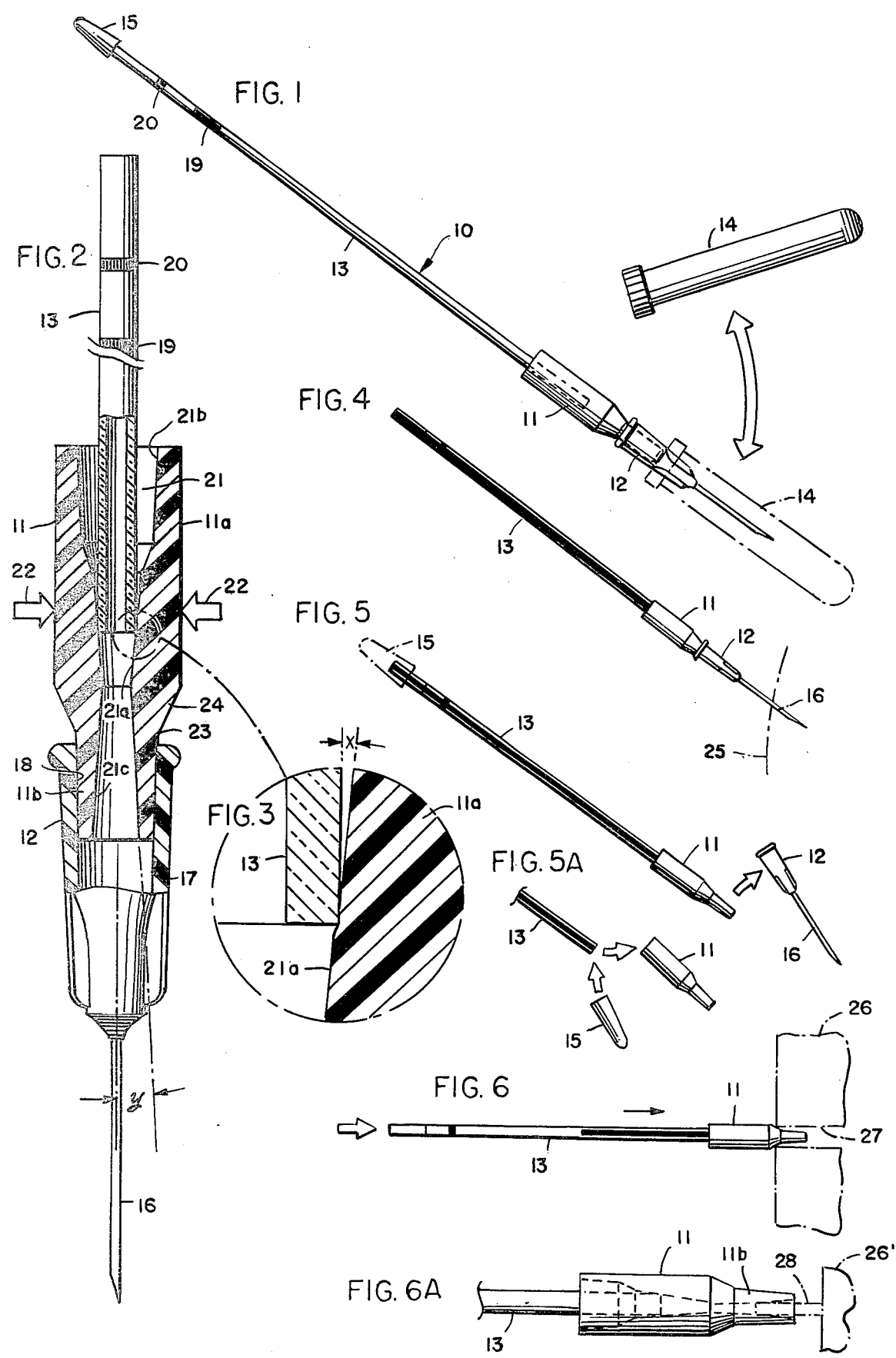

METHOD AND DEVICE FOR COLLECTING, TRANSPORTING, AND DELIVERING MICRO SAMPLES OF BLOOD

BACKGROUND AND SUMMARY

Arterial blood for diagnostic testing in blood gas analyzers is commonly collected by means of syringes, vacuum tubes, or capillary tubes, each of which presents substantial disadvantages and difficulties. Syringes must be airtight and, if formed of glass, usually require lubrication. The entire dead space between the needle and the plunger must be filled with a heparin solution, a procedure requiring considerable care to avoid small air bubbles that may cling to the barrel or to the plunger and prevent anerobic sampling. After collecting the blood, any residual air in the syringe must be expelled to prevent the loss of carbon dioxide from the blood by diffusion.

Although arterial blood can also be collected in heparinized vacuum tubes, the requirement that such tubes be filled completely with blood (to avoid a loss of $pCO_2$ and an increase in pH) renders such a procedure especially difficult. Also, there has been indications that utilizing a vacuum for drawing blood samples may under some circumstances tend to cause hemolysis.

The use of heparinized capillary tubes has the advantage over the other techniques of avoiding the collection of excessively large samples, a particularly important consideration in pediatric studies, but in other respects the procedures used with such capillary tubes involve the same problems of collecting, transporting, and delivering samples under substantially anerobic conditions.

A main object of this invention therefore lies in providing a method which greatly simplifies the procedures for sampling arterial (and venous) blood, and for doing so in a way that minimizes risks of exposure to air and increases the reproducibility and accuracy of test results. Another object is to provide a relatively safe, uncomplicated, inexpensive, and highly effective method for drawing micro samples of arterial or venous blood and for storing, transporting, and delivering such samples to suitable blood analysis equipment.

Briefly, the device includes a capillary tube, an adapter-handle detachably connected to the tube, and a hypodermic needle detachably mounted on the adapter-handle. A protective cover may extend over the needle, and at least one end cap is provided to seal the end (or ends) of the capillary tube after a blood sample is collected.

The adapter-handle is formed of resilient plastic material and has integral body and tip sections. A bore extends longitudinally through both sections with that portion of the bore within the body section tapering gradually inwardly at an angle of approximately 2 to 6 degrees measured from the axis of the adapter-handle. The tip of the adapter-handle has reduced outside cross sectional dimensions and is tapered both internally and externally. The external taper is that of a conventional Luer taper, permitting the tip to be inserted and retained within the hub of a standard hypodermic needle having a female Luer taper. The internal taper of the tip extends inwardly at an angle in the range of about 1 to 3 degrees and is dimensioned to receive and sealingly engage the inlet tubes of various models of commercially-available blood gas analyzers. Between the Luer-tapered outer surface of the tip and the gererally cylindrical outer surface of the body is a more sharply tapered surface of a frusto-conical intermediate section, such surface being adapted to engage and seal against the mouths of the inlet passages of other types of available blood gas analyzers.

In use, the heparin-coated capillary tube, the resilient adapter-handle, and the needle are assembled. A suitable artery or vein is punctured and the capillary tube is filled by reason of arterial or venous pressure. The free end of the capillary tube is then capped, thereby preventing blood from escaping from either end of the capillary tube when the needle is withdrawn from the puncture site. If analysis is to occur immediately, then the user simply mixes the sample with the heparin within the tube, detaches and discards the needle, couples the tip portion of the adapter-handle to a blood analyzer, removes the cap, and allows the micro sample to be drawn into the analyzer. If, on the other hand, any delay is to be encountered before analysis, the user detaches (and discards) the adapter-handle, replaces it with an end cap, and then, following mixing, transit and/or storage, removes both caps, replacing one with a fresh adapter-handle for delivering the sample to the inlet of a blood analyzer in the manner already described.

Other advantages, objects, and features of the invention will become apparent from the drawings and specification.

DRAWINGS

FIG. 1 is a side view of a device embodying this invention, the device being shown with its needle cover removed (but with phantom lines showing its attached position) for clarity of illustration.

FIG. 2 is an enlarged longitudinal side view, taken partly in section, of the device.

FIG. 3 is a still further enlarged fragmentary view of an indicated portion of FIG. 2 illustrating the functional relationship between the parts.

FIG. 4 illustrates a first step in the method during which blood is drawn into the microcapillary tube.

FIG. 5 illustrates a further step in which the needle is removed and the distal end of the capillary tube is capped.

FIG. 5A depicts a further step which may be used when access to a blood analyzer is delayed.

FIG. 6 represents a further step of delivering the blood to an analyzer having a female connector forming the inlet thereof.

FIG. 6A depicts the delivery step when the analyzer is provided with a male connector at the inlet thereof.

DETAILED DESCRIPTION

Referring to the drawings, the numeral 10 generally designates a device comprising an adapter-handle 11, a needle assembly 12, and a microcapillary tube 13. Such components may be supplied to the user in assembled form as shown, or they may be supplied as separate parts to be assembled by the user. In either case, a suitable cover 14 should be attached to the needle 12 to maintain sterility of the needle until use. An end cap 15 may be fitted upon the distal end of the capillary tube, and the entire assembly may be supplied in sterile condition within a suitable wrapper (not shown).

The needle assembly 12, shown most clearly in FIG. 2, is conventional in construction and includes a hollow needle 16 secured to a cup-shaped hub 17. In the illustration given, hub 17 is formed of rigid plastic such as, for example, polystyrene, although it is to be understood that other materials such as metals might be used. The open end of the hub provides the entrance to a tapered cavity 18 dimensioned to receive and frictionally engage the tip of adapter 11. The inward taper of the cavity 18 is commonly referred to as a standard Luer taper, meaning that the hub will mate tightly with a tapered syringe tip identified by the name of its originator. Such taper is described in Federal Specification GG-N-196 and corresponds to an angle approximately 1°43'6" measured from the axis of the needle assembly 12 (or an included angle of about 3°26'12"). In a preferred embodiment, the metal needle 16 should be of relatively small gauge (No. 25 or less) and the opening at the mouth of the cavity should be approximately 0.165 of an inch in diameter.

The tubular needle cover 14 is entirely conventional and serves simply to protect the pointed hollow needle 16 as well as objects which the needle might otherwise contact, and to help maintain sterility of the needle. The cover may be formed of any of a variety of rigid or semi-rigid polymers such as, for example, polypropylene or other polyolefins.

The microcapillary tube is also conventional, being formed of glass and usually being of a standard length of 100 millimeters. Such a tube has a through-bore which is precisely dimensioned to contain a sample of predetermined volume, ordinarily either 100 or 200 microliters ($\mu l$). Color coded bands 19 and 20 indicate to the user both the capacity of the tube and the fact that its interior surfaces have been heparinized to prevent coagulation of a blood sample drawn into the tube.

End cap 15 is preferably formed of ethyl vinyl acetate, silicone rubber, or some other suitable resilient plastic material and defines a tapered cavity for snugly and sealingly receiving the end of glass capillary tube 13. While only a single end cap is needed in certain uses of the blood collection device, a second identical end cap may be supplied to the user where temporary sealing of the opposite end of the capillary tube is also deemed necessary or desirable.

The adapter-handle 11 is also formed from a relatively soft resilient elastomer such as ethyl vinyl acetate or silicone rubber and is composed of integral body and tip sections 11a and 11b, respectively. A bore 21 extends through the adapter with that portion 21a of the bore within body section 11a tapering gradually inwardly for receiving and frictionally retaining one end of microcapillary tube 13. The gradual taper of bore portion 21a and the resiliency of the material from which the adapter is formed not only insure that a tight frictional seal will be formed between the end of the capillary tube and the adapter but also permits the adapter to form such engagement with standard capillary tubes of different diameters and capacities. It will be noted from the enlarged view of FIG. 3 that slight deformation of the wall of the adapter takes place when the end of a capillary tube is formed into the tapered bore portion 21a, such deformation assisting in the frictional retention of the capillary tube without danger of chipping or fracturing that tube. In addition, retention of a capillary tube by the adapter is enhanced by the squeezing force normally applied (in the direction of arrows 22 in FIG. 2) when the resilient adapter is gripped between the fingers and used as a handle. The angle of taper x (FIG. 3) measured from the longitudinal axis of the adapter should fall within 2° to 6° and should encompass a range of diameters of at least 0.08 to 0.10 of an inch. In a preferred embodiment, an angle of taper of 4° and a size range of approximately 0.070 to 0.110 of an inch have been found effective for coupling the adapter to standard microcapillary tubes.

In some cases it may be desirable to draw a larger sample of arterial or venous blood and for that purpose the tapered bore of the body section 11a may be stepped outwardly to provide an enlarged entrance portion 21b. Bore portion 21b has a Luer taper similar to that of hub cavity 18 and, consequently, is adapted to mate with the Luer tip of a standard syringe. Like the cavity 18 of the needle hub, bore portion 21b should have a maximum diameter at its mouth of approximately 0.165 of an inch.

The tip section 11b of the adapter is reduced in outside dimensions and has a standard male Luer taper allowing the distal portion of the tip to be received tightly within the cavity 18 of the needle hub. The angle of taper of the tip's outer surface should match closely the angle of inside taper of the hub with the maximum outside diameter of the tip at point 23 exceeding the inside diameter at the mouth of cavity 18. A differential of at least 0.003 of an inch should be provided (0.005 preferred) to insure a snug fluid-tight friction fit between the parts.

Beyond the Luer tapered outer surface, between point 23 and the generally cylindrical outer surface of body section 11a, the tip is provided with a flared or frusto-conical outer surface 24. The angle of that frusto-conical surface, measured from the axis of the adapter, should fall within the general range of 10° to 30°, an angle of approximately 20° being found particularly effective. As described hereinafter, the frusto-conical surface is not merely a transitional surface between the Luer taper of the tip and the cylindrical surface of the body; it provides an inclined stop for limiting the extent of insertion of the adapter into the inlet port of a blood analyzer, and for sealingly engaging that port when delivery of a sample to such an analyzer takes place.

It will be noted that the internal and external longitudinal surfaces of the tip section 11b are reversely tapered; that is, in addition to having a Luer taper along its outer surface the tip has a reversely-tapered bore portion 21c which gradually and progressively increases in size towards the free end of the tip section. The angle of taper y (FIG. 2) should fall generally within the range of 1° to 3° measured from the longitudinal axis of the adapter, the preferred angle of taper being approximately 2°. At its mouth the bore portion 21c should have a diameter of at least 0.08 of an inch, a preferred dimension being about 0.09 of an inch. As shown, bore portion 21c tapers smoothly and gradually inwardly to merge with bore portion 21a of body section 11a.

For use, the device 10 may be supplied in assembled condition as shown in FIG. 1. Alternatively, the device may be supplied in disassembled condition, requiring interfitting of the major components by the user. Assuming that the device is in the assembled condition of FIG. 1, the user removes end cap 15, detaches the protective needle cover 14, and, holding the device by means of the resilient adapter-handle 11, inserts the sterile needle 16 into the blood vessel from which the sample is to be taken. For blood gas analysis arterial blood is preferred. Such blood may be obtained by inserting the fine-gauge needle 16 into an artery such as the brachial, radial, femoral, or jugular arteries. FIG. 4 depicts the sampling step, the outline of the patient's body being generally represented by line 25 and the transparent collection tube shown to be filled with blood taken from the patient. Entry of the needle into an artery is confirmed by the pulsatile filling of the bore of the glass capillary tube, such filling action generally being completed within three seconds and occuring by reason of arterial (or venous) pressure. The user then withdraws the needle and immediately caps the remote end of the capillary tube with cap 15 (FIG. 5). Still holding the device by means of the adapter-handle, the user detaches (and discards) the needle assembly 12. If the blood analyzing equipment is close at hand, the adapter is then simply coupled to the inlet connector of the analyzer to allow the collected blood sample to be drawn into the analyzer where it is tested (FIGS. 6 and 6A).

After taking a sample, and before introducing that sample into an analyzer, a user should make sure that the sample is thoroughly mixed with the heparin salt coating the inside surfaces of the capillary tube. A suitable magnetic stirrer, commonly referred to as a "flea", may be inserted into the bore of the tube and reciprocated therein by means of an external magnet. Particularly effective results may be achieved where end cap 15 is formed and used as set forth in my copending U.S. Pat. application Ser. No. 10,234, filed Feb. 8, 1979, the disclosure of which is incorporated by reference herein, so that upon completion of the mixing step the flea may be captured and removed by means of the cap, thereby preventing the possibility that such a flea might be left within the capillary tube and be drawn accidentally into the blood analyzer.

In FIG. 6 the numeral 26 generally designates that type of commercially-available blood analyzer having an inlet port 27, the mouth of which is engagable with the tip section of the adapter 11 to provide a temporary seal as the blood sample is aspirated from the capillary tube into the machine. The frusto-conical outer surface 24 of the adapter is particularly effective in forming such a seal with the mouth of the instrument and for limiting the extent of insertion of the resilient adapter into the inlet.

FIG. 6A schematically depicts a different type of blood analyzer 26' in which the inlet takes the form of a protruding nipple or tube 28 having an outside diameter of approximately 0.08 of an inch. In delivering a blood sample to such an analyzer, the user, holding the device by its resilient adapter 11, simply fits the internally tapered tip section 11b on to the inlet tube 28 and allows the blood sample to be drawn into the machine.

In those cases where the blood analyzer is remote from the collection site, adapter-handle 11 may be removed from the filled capillary tube 13 and replaced by a second end cap 15 (FIG. 5A). With both ends of the capillary tube so capped, the collected sample may be mixed, transported, and temporarily stored under refrigeration. Upon arrival at the blood analyzer, one of the end caps is removed and replaced by a fresh adapter 11. The procedure represented in FIG. 6 or 6A is then performed with the distal end cap 15 removed from the capillary tube to permit aspiration of the blood sample into the analyzer.

It is believed evident from the foregoing that the adapter 11 is constructed to perform a multiplicity of functions. In addition to its coupling functions the adapter serves as a resilient handle. In the operations depicted in FIGS. 4, 5, 6, and 6A, the user grips the sampling device by holding the resilient adapter between his fingers. As already described, the squeezing forces tend to assist in maintaining the capillary tube and adapter in interconnected relation. In addition, the danger of breakage of the fragile capillary tube, and the risks of possible contamination of the user, are reduced. For example, should a patient move suddenly during arterial or venous puncture, the resilient handle provides limited articulation between the rigid glass tube 13 and the needle assembly 12, thereby reducing the chances of breakage of either rigid part, and, should such breakage happen to occur, the handle serves as a protective sheath between the fractured tube and the user's fingers to prevent injury and possible contamination.

While in the foregoing I have disclosed an embodiment of this invention in considerable detail for purposes of illustration it will be understood by those skilled in the art that many of these details may be varied without departing from the spirit and scope of the invention.

I claim:

1. A method for collecting a micro sample of blood and delivering the same to an analyzer for laboratory analysis, using an open-ended heparinized capillary tube having one end received within the bore of a tubular adapter, said adapter having a tip with a male Luer, and a hypodermic needle having a hub with a female Luer taper frictionally and releasably receiving said adapter tip, comprising the steps of inserting said needle into a blood vessel of a patient and collecting a sample of blood in said capillary tube, disconnecting said needle hub from said adapter and capping the end of said capillary tube remote from said one end thereof, and then coupling said adapter to the inlet of a blood analyzer and removing said cap from said capillary tube to allow the blood sample to flow from said tube into said analyzer.

2. The method of claim 1 in which said coupling step is performed by introducing said tapered tip of said adapter into an inlet opening of a blood analyzer to form a fluid-tight seal therebetween.

3. The method of claim 1 in which the bore of the tip of said adapter has a female taper, said coupling step being performed by inserting an inlet tube of a blood analyzer into the bore of said tip to form a fluid-tight seal therebetween.

4. The method of claim 1 in which said needle is inserted into an artery.

5. The method of claim 1 in which said needle is inserted into a vein.

6. The method of claim 1 in which said adapter is formed of resilient, flexible plastic material and in which said inserting, disconnecting, and coupling steps include gripping said adapter between a user's fingers, thereby increasing the contact force between said adapter and said capillary tube.

7. A method for collecting a micro sample of blood and delivering the same to an analyzer for laboratory analysis, using an open-ended heparinized capillary tube having one end frictionally received within the bore of a tubular adapter, said adapter having a tip with a male Luer taper, and a hypodermic needle having a hub with a female Luer taper frictionally and releasably receiving said adapter tip, comprising the steps of inserting said hypodermic needle into a blood vessel of a patient to fill said capillary tube with a sample of the patient's blood, withdrawing the needle from said vessel and capping the end of said capillary tube remote from said one end to retain said sample within said tube, transporting said sample to a blood analyzer in said capped capillary tube, and thereafter uncapping said tube and discharging said sample into said analyzer.

8. The method of claim 7 in which said sample is discharged into said analyzer by coupling said tip of said adapter to the inlet of the analyzer to place said capillary tube in flow communication with said inlet.

9. The method of claim 7 in which there is the further step of disconnecting said adapter from said one end of said capillary tube prior to said transporting step.

10. The method of claim 9 in which there is the further step of capping said one end of said capillary tube after said needle is disconnected therefrom and prior to said transporting step.

11. The method of claim 9 in which there is the further step of attaching a second adapter to said one end of said capillary tube after said transporting step, said sample being discharged into said analyzer by coupling said second adapter to the inlet of said analyzer.

* * * * *

UNITED STATES PATENT AND TRADEMARK OFFICE
CERTIFICATE OF CORRECTION

PATENT NO. : 4,263,922

DATED : April 28, 1981

INVENTOR(S) : Fred K. White

It is certified that error appears in the above-identified patent and that said Letters Patent are hereby corrected as shown below:

In the title, cancel "AND DEVICE".

Signed and Sealed this

First Day of September 1981

[SEAL]

Attest:

Attesting Officer

GERALD J. MOSSINGHOFF

Commissioner of Patents and Trademarks